(12) United States Patent
Schaller et al.

(10) Patent No.: US 8,394,114 B2
(45) Date of Patent: Mar. 12, 2013

(54) SURGICAL CONNECTION APPARATUS AND METHODS

(75) Inventors: Laurent Schaller, Los Altos, CA (US);
Liem Ho, Mountain View, CA (US);
Tom Breton, Palo Alto, CA (US)

(73) Assignee: Medtronic, Inc., Minneapolis, MN (US)

( * ) Notice: Subject to any disclaimer, the term of this patent is extended or adjusted under 35 U.S.C. 154(b) by 2197 days.

(21) Appl. No.: 10/672,009

(22) Filed: Sep. 26, 2003

(65) Prior Publication Data

US 2005/0070924 A1 Mar. 31, 2005

(51) Int. Cl.
*A61B 17/08* (2006.01)

(52) U.S. Cl. ........................................ 606/153; 606/142

(58) Field of Classification Search .................. 606/124, 606/151–155, 149, 159, 158, 148, 222, 157, 606/217, 219, 186–189; 600/564–567
See application file for complete search history.

(56) References Cited

U.S. PATENT DOCUMENTS

| 43,098 | A | 6/1864 | Cooper |
| 655,190 | A | 8/1900 | Bramson |
| 1,087,186 | A | 2/1914 | Scholfield |
| 1,167,014 | A | 1/1916 | O'Brien |
| 1,583,271 | A | 5/1926 | Biro |
| 1,625,602 | A | 4/1927 | Gould et al. |
| 1,867,624 | A | 7/1932 | Hoffman |
| 2,201,610 | A | 5/1940 | Dawson |
| 2,240,330 | A | 4/1941 | Flagg et al. |
| 2,256,382 | A | 9/1941 | Dole |
| 2,264,679 | A | 12/1941 | Ravel |
| 2,413,142 | A | 12/1946 | Jones et al. |
| 2,430,293 | A | 4/1947 | Howells |
| 2,505,358 | A | 4/1950 | Gusberg et al. |
| 2,516,710 | A | 7/1950 | Mascolo |
| 2,715,486 | A | 8/1955 | Marcoff-Moghadam |
| 2,890,519 | A | 6/1959 | Storz, Jr. |
| 2,940,452 | A | 6/1960 | Smialowski |
| 3,055,689 | A | 9/1962 | Jorgensen |
| 3,057,355 | A | 10/1962 | Smialowski |
| 3,082,426 | A | 3/1963 | Miles |
| 3,802,438 | A | 3/1963 | Miles |
| 3,143,742 | A | 8/1964 | Cromie |
| 3,150,379 | A | 9/1964 | Brown |
| 3,180,337 | A | 4/1965 | Smialowski |
| 3,249,104 | A | 5/1966 | Hohnstein |
| 3,274,658 | A | 9/1966 | Pile |
| 3,452,742 | A | 7/1969 | Muller |

(Continued)

FOREIGN PATENT DOCUMENTS

| DE | 0219999 | 3/1910 |
| DE | 0377052 | 6/1923 |

(Continued)

OTHER PUBLICATIONS

"VCS Clip Applier System," published in 1995 by Auto Suture Company, a Division of U.S. Surgical Corporation (8 pages).

(Continued)

*Primary Examiner* — Tuan V Nguyen

(57) ABSTRACT

Surgical connection apparatus comprises a support structure, a plurality of clips, which can be self-closing clips, each clip being releasably coupled to the support structure, and a plurality of barbs, each barb being coupled to the support structure, the barbs being separate from the clips, which are ejectable from the support structure independently of the barbs.

18 Claims, 9 Drawing Sheets

U.S. PATENT DOCUMENTS

| | | |
|---|---|---|
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,776,237 A | 12/1973 | Hill et al. |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razgulov et al. |
| 3,910,281 A | 10/1975 | Kletschka et al. |
| 3,958,576 A | 5/1976 | Komiya |
| 3,976,079 A | 8/1976 | Samuels |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,657,019 A | 4/1987 | Walsh et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,733,664 A | 3/1988 | Kirsch et al. |
| 4,771,775 A | 9/1988 | Walsh et al. |
| 4,787,386 A | 11/1988 | Walsh et al. |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,917,087 A | 4/1990 | Walsh et al. |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,100,418 A | 3/1992 | Yoon |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |
| 5,192,294 A | 3/1993 | Blake |
| 5,196,022 A | 3/1993 | Bilweis |
| 5,201,880 A | 4/1993 | Wright et al. |
| 5,207,694 A | 5/1993 | Broome |
| 5,217,027 A | 6/1993 | Hermens |
| 5,219,358 A | 6/1993 | Bendel et al. |
| 5,221,259 A | 6/1993 | Weldon et al. |
| 5,222,961 A | 6/1993 | Nakao et al. |
| 5,222,976 A | 6/1993 | Yoon |
| 5,234,447 A | 8/1993 | Kaster et al. |
| 5,236,440 A | 8/1993 | Hlavacek |
| 5,242,456 A | 9/1993 | Nash et al. |
| 5,242,457 A | 9/1993 | Akopov et al. |
| 5,246,443 A | 9/1993 | Mai |
| 5,250,053 A | 10/1993 | Snyder |
| 5,258,011 A | 11/1993 | Drews |
| 5,261,917 A | 11/1993 | Hasson et al. |
| 5,269,783 A | 12/1993 | Sander |
| 5,269,809 A | 12/1993 | Hayhurst et al. |
| 5,282,825 A | 2/1994 | Muck et al. |
| 5,290,289 A | 3/1994 | Sanders et al. |
| 5,304,117 A | 4/1994 | Wilk |
| 5,304,204 A | 4/1994 | Bregen |
| 5,306,296 A | 4/1994 | Wright et al. |
| 5,312,436 A | 5/1994 | Coffey et al. |
| 5,314,468 A | 5/1994 | Martinez |
| 5,330,503 A | 7/1994 | Yoon |
| 5,336,233 A | 8/1994 | Chen |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |

| | | | | | |
|---|---|---|---|---|---|
| 5,355,897 A | 10/1994 | Pietrafitta et al. | 5,697,943 A | 12/1997 | Sauer et al. |
| 5,356,424 A | 10/1994 | Buzerak et al. | 5,700,270 A | 12/1997 | Peyser et al. |
| 5,366,459 A | 11/1994 | Yoon | 5,700,271 A | 12/1997 | Whitfield et al. |
| 5,366,462 A | 11/1994 | Kaster et al. | 5,702,412 A | 12/1997 | Popov et al. |
| 5,366,479 A | 11/1994 | McGarry et al. | 5,707,362 A | 1/1998 | Yoon |
| 5,374,268 A | 12/1994 | Sander | 5,707,380 A | 1/1998 | Hinchliffe et al. |
| 5,382,259 A | 1/1995 | Phelps et al. | 5,709,693 A | 1/1998 | Taylor |
| 5,383,904 A | 1/1995 | Totakura et al. | 5,709,695 A | 1/1998 | Northrup, III |
| 5,403,331 A | 4/1995 | Chesterfield | 5,715,987 A | 2/1998 | Kelley et al. |
| 5,403,333 A | 4/1995 | Kaster et al. | 5,720,755 A | 2/1998 | Dakov |
| 5,403,338 A | 4/1995 | Milo | 5,720,756 A | 2/1998 | Green et al. |
| 5,403,346 A | 4/1995 | Loeser | 5,725,537 A | 3/1998 | Green et al. |
| 5,417,700 A | 5/1995 | Egan | 5,725,539 A | 3/1998 | Matern |
| 5,423,821 A | 6/1995 | Pasque | 5,725,542 A | 3/1998 | Yoon |
| 5,431,666 A | 7/1995 | Sauer et al. | 5,728,135 A | 3/1998 | Bregen et al. |
| 5,437,680 A | 8/1995 | Yoon | 5,732,872 A | 3/1998 | Bolduc et al. |
| 5,437,681 A | 8/1995 | Meade et al. | 5,735,290 A | 4/1998 | Sterman et al. |
| 5,437,685 A | 8/1995 | Blasnik | 5,749,879 A | 5/1998 | Middleman et al. |
| 5,439,479 A | 8/1995 | Schichman et al. | 5,755,778 A | 5/1998 | Kleshinski |
| 5,445,167 A | 8/1995 | Yoon et al. | 5,766,189 A | 6/1998 | Matsumo |
| 5,445,644 A | 8/1995 | Pietrafitta et al. | 5,769,870 A | 6/1998 | Salahich et al. |
| 5,450,860 A | 9/1995 | O'Connor | 5,779,718 A | 7/1998 | Green et al. |
| 5,452,733 A | 9/1995 | Sterman et al. | 5,782,397 A | 7/1998 | Koukline |
| 5,454,834 A | 10/1995 | Boebel et al. | 5,782,844 A | 7/1998 | Yoon et al. |
| 5,456,246 A | 10/1995 | Schmiedling et al. | 5,797,920 A | 8/1998 | Kim |
| 5,462,561 A | 10/1995 | Voda | 5,797,933 A | 8/1998 | Snow et al. |
| 5,474,557 A | 12/1995 | Mai | 5,797,934 A | 8/1998 | Rygaard |
| 5,480,405 A | 1/1996 | Yoon | 5,797,960 A | 8/1998 | Stevens et al. |
| 5,486,187 A | 1/1996 | Schenck | 5,799,661 A | 9/1998 | Boyd et al. |
| 5,486,197 A | 1/1996 | Le et al. | 5,799,857 A | 9/1998 | Robertson et al. |
| 5,488,958 A | 2/1996 | Topel et al. | 5,810,848 A | 9/1998 | Hayhurst |
| 5,496,334 A | 3/1996 | Klundt et al. | 5,810,851 A | 9/1998 | Yoon |
| 5,499,990 A | 3/1996 | Schulken et al. | 5,810,853 A | 9/1998 | Yoon |
| 5,500,000 A | 3/1996 | Feagin et al. | 5,810,882 A | 9/1998 | Bolduc et al. |
| 5,522,884 A | 6/1996 | Wright | 5,817,113 A | 10/1998 | Gifford, III et al. |
| 5,527,342 A | 6/1996 | Pietrzak et al. | 5,820,631 A | 10/1998 | Nobles |
| 5,533,236 A | 7/1996 | Tseng | 5,824,002 A | 10/1998 | Gentelia et al. |
| 5,538,509 A | 7/1996 | Dunlap et al. | 5,824,008 A | 10/1998 | Bolduc et al. |
| 5,545,214 A | 8/1996 | Stevens | 5,827,265 A | 10/1998 | Glinsky et al. |
| 5,549,619 A | 8/1996 | Peters et al. | 5,827,316 A | 10/1998 | Young et al. |
| 5,556,411 A | 9/1996 | Taoda et al. | 5,830,221 A | 11/1998 | Stein et al. |
| 5,562,685 A | 10/1996 | Mollenauer et al. | 5,830,222 A | 11/1998 | Makower |
| 5,569,205 A | 10/1996 | Hart et al. | 5,833,698 A | 11/1998 | Hinchliffe |
| 5,569,274 A | 10/1996 | Rapacki et al. | 5,849,019 A | 12/1998 | Yoon |
| 5,569,301 A | 10/1996 | Granger et al. | 5,851,216 A | 12/1998 | Allen |
| 5,571,119 A | 11/1996 | Atala | 5,855,614 A | 1/1999 | Stevens et al. |
| 5,571,175 A | 11/1996 | Vanney et al. | 5,868,702 A | 2/1999 | Stevens et al. |
| 5,582,616 A | 12/1996 | Bolduc et al. | 5,868,763 A | 2/1999 | Spence et al. |
| 5,582,619 A | 12/1996 | Ken | 5,871,528 A | 2/1999 | Camps et al. |
| 5,584,879 A | 12/1996 | Reimold et al. | 5,879,371 A | 3/1999 | Gardiner et al. |
| 5,586,983 A | 12/1996 | Sanders et al. | 5,881,943 A | 3/1999 | Heck et al. |
| 5,591,179 A | 1/1997 | Edelstein | 5,882,340 A | 3/1999 | Yoon |
| 5,593,414 A | 1/1997 | Shipp et al. | 5,891,130 A | 4/1999 | Palermo et al. |
| 5,593,424 A | 1/1997 | Northrupp, III | 5,891,160 A | 4/1999 | Williamson, IV et al. |
| 5,597,378 A | 1/1997 | Jervis | 5,893,369 A | 4/1999 | LeMole |
| 5,601,571 A | 2/1997 | Moss | 5,893,865 A | 4/1999 | Swindle et al. |
| 5,601,572 A | 2/1997 | Middleman et al. | 5,893,886 A | 4/1999 | Zegdi et al. |
| 5,601,600 A | 2/1997 | Ton | 5,895,394 A | 4/1999 | Kienzle et al. |
| 5,603,718 A | 2/1997 | Xu | 5,904,697 A | 5/1999 | Gifford, III et al. |
| 5,607,435 A | 3/1997 | Sachdeva et al. | 5,908,428 A | 6/1999 | Scirica et al. |
| 5,609,608 A | 3/1997 | Bennett et al. | 5,911,352 A | 6/1999 | Racenet et al. |
| 5,628,757 A | 5/1997 | Hasson | 5,919,207 A | 7/1999 | Taheri |
| 5,630,540 A | 5/1997 | Blewett | 5,921,995 A | 7/1999 | Kleshinski |
| 5,632,752 A | 5/1997 | Buelna | 5,931,842 A | 8/1999 | Goldsteen et al. |
| 5,632,753 A | 5/1997 | Loeser | 5,941,434 A | 8/1999 | Green |
| 5,643,295 A | 7/1997 | Yoon | 5,941,442 A | 8/1999 | Geiste et al. |
| 5,643,305 A | 7/1997 | Al-Tameem | 5,941,888 A | 8/1999 | Wallace et al. |
| 5,645,568 A | 7/1997 | Chervitz et al. | 5,941,908 A | 8/1999 | Goldsteen et al. |
| 5,653,718 A | 8/1997 | Yoon | 5,944,730 A | 8/1999 | Nobles et al. |
| 5,658,312 A | 8/1997 | Green et al. | 5,951,576 A | 9/1999 | Wakabayashi |
| 5,660,186 A | 8/1997 | Bachir | 5,951,600 A | 9/1999 | Lemelson |
| 5,665,109 A | 9/1997 | Yoon | 5,954,735 A | 9/1999 | Rygaard |
| 5,669,918 A | 9/1997 | Balazs et al. | 5,957,363 A | 9/1999 | Heck |
| 5,676,670 A | 10/1997 | Kim | 5,957,938 A | 9/1999 | Zhu et al. |
| 5,683,417 A | 11/1997 | Cooper | 5,957,940 A | 9/1999 | Tanner et al. |
| 5,690,662 A | 11/1997 | Chiu et al. | 5,961,481 A | 10/1999 | Sterman et al. |
| 5,695,504 A | 12/1997 | Gifford, III et al. | 5,961,539 A | 10/1999 | Northrup, III et al. |
| 5,695,505 A | 12/1997 | Yoon | 5,964,772 A | 10/1999 | Bolduc et al. |
| 5,697,913 A | 12/1997 | Sierocuk et al. | 5,964,782 A | 10/1999 | Lafontaine et al. |

| Patent | Kind | Date | Name | | Patent | Kind | Date | Name |
|---|---|---|---|---|---|---|---|---|
| 5,972,024 | A | 10/1999 | Northrup, III et al. | | 6,346,112 | B2 | 2/2002 | Adams |
| 5,976,159 | A | 11/1999 | Bolduc et al. | | 6,350,269 | B1 | 2/2002 | Shipp et al. |
| 5,976,161 | A | 11/1999 | Kirsch et al. | | 6,352,543 | B1 | 3/2002 | Cole |
| 5,976,164 | A | 11/1999 | Bencini et al. | | 6,358,258 | B1 * | 3/2002 | Arcia et al. .............. 606/139 |
| 5,976,178 | A | 11/1999 | Goldsteen et al. | | 6,361,559 | B1 | 3/2002 | Houser et al. |
| 5,984,917 | A | 11/1999 | Fleischman et al. | | 6,368,348 | B1 | 4/2002 | Gabbay |
| 5,984,959 | A | 11/1999 | Robertson et al. | | 6,371,964 | B1 | 4/2002 | Vargas et al. |
| 5,989,242 | A | 11/1999 | Saadat et al. | | 6,387,105 | B1 | 5/2002 | Gifford, III et al. |
| 5,989,268 | A | 11/1999 | Pugsley, Jr. et al. | | 6,391,038 | B2 | 5/2002 | Vargas et al. |
| 5,989,276 | A | 11/1999 | Houser et al. | | 6,402,764 | B1 | 6/2002 | Hendricksen et al. |
| 5,989,278 | A | 11/1999 | Mueller | | 6,402,765 | B1 | 6/2002 | Monassevitch et al. |
| 5,993,468 | A | 11/1999 | Rygaard | | 6,406,492 | B1 | 6/2002 | Lytle |
| 5,997,556 | A | 12/1999 | Tanner | | 6,406,493 | B1 | 6/2002 | Tu et al. |
| 6,001,110 | A | 12/1999 | Adams | | 6,409,739 | B1 | 6/2002 | Nobles et al. |
| 6,007,544 | A | 12/1999 | Kim | | 6,409,758 | B2 | 6/2002 | Stobie et al. |
| 6,010,531 | A | 1/2000 | Donlon et al. | | 6,416,527 | B1 | 7/2002 | Berg et al. |
| 6,013,084 | A | 1/2000 | Ken et al. | | 6,418,597 | B1 | 7/2002 | Deschenes et al. |
| 6,022,367 | A | 2/2000 | Sherts | | 6,419,658 | B1 | 7/2002 | Restelli et al. |
| 6,024,748 | A | 2/2000 | Manzo et al. | | 6,419,681 | B1 | 7/2002 | Vargas et al. |
| 6,032,849 | A | 3/2000 | Mastri et al. | | 6,419,695 | B1 | 7/2002 | Gabbay |
| 6,033,419 | A | 3/2000 | Hamblin, Jr. et al. | | 6,425,900 | B1 | 7/2002 | Knodel et al. |
| 6,036,699 | A | 3/2000 | Andreas et al. | | 6,428,550 | B1 | 8/2002 | Vargas et al. |
| 6,036,703 | A | 3/2000 | Evans et al. | | 6,428,555 | B1 | 8/2002 | Koster, Jr. |
| 6,036,710 | A | 3/2000 | McGarry et al. | | 6,451,034 | B1 | 9/2002 | Gifford, III et al. |
| 6,042,607 | A | 3/2000 | Williamson et al. | | 6,451,048 | B1 | 9/2002 | Berg et al. |
| 6,056,751 | A | 5/2000 | Fenton | | 6,461,320 | B1 | 10/2002 | Yencho et al. |
| 6,063,070 | A | 5/2000 | Eder | | 6,461,365 | B2 | 10/2002 | Bolduc et al. |
| 6,066,148 | A | 5/2000 | Rygaard | | 6,475,222 | B1 | 11/2002 | Berg et al. |
| 6,068,637 | A | 5/2000 | Popov et al. | | 6,478,804 | B2 | 11/2002 | Vargas et al. |
| 6,074,401 | A | 6/2000 | Gardiner et al. | | 6,485,496 | B1 | 11/2002 | Suyker et al. |
| 6,074,418 | A | 6/2000 | Buchanan et al. | | 6,491,707 | B2 | 12/2002 | Makower et al. |
| 6,077,291 | A | 6/2000 | Das | | 6,497,671 | B2 | 12/2002 | Ferrera et al. |
| 6,080,114 | A | 6/2000 | Russin | | 6,497,710 | B2 | 12/2002 | Yencho et al. |
| 6,083,237 | A | 7/2000 | Huitema et al. | | 6,514,265 | B2 | 2/2003 | Ho et al. |
| 6,106,538 | A | 8/2000 | Shiber | | 6,517,558 | B2 | 2/2003 | Gittings et al. |
| 6,110,188 | A | 8/2000 | Narciso, Jr. | | 6,524,338 | B1 | 2/2003 | Gundry |
| 6,113,611 | A | 9/2000 | Allen et al. | | 6,533,812 | B2 | 3/2003 | Swanson et al. |
| 6,113,612 | A | 9/2000 | Swanson et al. | | 6,537,288 | B2 | 3/2003 | Vargas et al. |
| 6,120,524 | A | 9/2000 | Taheri | | 6,547,799 | B2 | 4/2003 | Hess et al. |
| 6,132,438 | A | 10/2000 | Fleischmann et al. | | 6,551,332 | B1 | 4/2003 | Nguyen et al. |
| 6,139,540 | A | 10/2000 | Rost et al. | | 6,562,053 | B2 | 5/2003 | Schulze et al. |
| 6,143,004 | A | 11/2000 | Davis et al. | | 6,572,626 | B1 | 6/2003 | Knodel et al. |
| 6,149,658 | A | 11/2000 | Gardiner et al. | | 6,575,985 | B2 | 6/2003 | Knight et al. |
| 6,152,935 | A | 11/2000 | Kammerer et al. | | 6,589,255 | B2 | 7/2003 | Schulze et al. |
| 6,152,937 | A | 11/2000 | Peterson et al. | | 6,607,541 | B1 | 8/2003 | Gardiner et al. |
| 6,159,165 | A | 12/2000 | Ferrera et al. | | 6,607,542 | B1 | 8/2003 | Wild et al. |
| 6,159,225 | A | 12/2000 | Makower | | 6,613,059 | B2 | 9/2003 | Schaller et al. |
| 6,165,183 | A | 12/2000 | Kuehn et al. | | 6,623,494 | B1 | 9/2003 | Blatter |
| 6,165,185 | A | 12/2000 | Shennib et al. | | 6,626,920 | B2 | 9/2003 | Whayne |
| 6,171,320 | B1 | 1/2001 | Monassevitch | | 6,629,988 | B2 | 10/2003 | Weadock |
| 6,171,321 | B1 | 1/2001 | Gifford, III et al. | | 6,635,214 | B2 | 10/2003 | Rapacki et al. |
| 6,176,413 | B1 | 1/2001 | Heck et al. | | 6,641,593 | B1 | 11/2003 | Schaller et al. |
| 6,176,864 | B1 | 1/2001 | Chapman | | 6,648,900 | B2 | 11/2003 | Fleischman et al. |
| 6,179,840 | B1 | 1/2001 | Bowman | | 6,651,670 | B2 | 11/2003 | Rapacki et al. |
| 6,179,848 | B1 | 1/2001 | Solem | | 6,651,672 | B2 | 11/2003 | Roth |
| 6,179,849 | B1 | 1/2001 | Yencho et al. | | 6,652,540 | B1 | 11/2003 | Cole et al. |
| 6,183,512 | B1 | 2/2001 | Howanec et al. | | 6,652,541 | B1 | 11/2003 | Vargas et al. |
| 6,190,373 | B1 | 2/2001 | Palermo et al. | | 6,652,544 | B2 | 11/2003 | Houser et al. |
| 6,190,396 | B1 | 2/2001 | Whitin et al. | | 6,660,015 | B1 | 12/2003 | Berg et al. |
| 6,193,733 | B1 | 2/2001 | Adams | | 6,669,708 | B1 | 12/2003 | Nissenbaum et al. |
| 6,193,734 | B1 | 2/2001 | Bolduc et al. | | 6,673,084 | B1 | 1/2004 | Peterson et al. |
| 6,197,037 | B1 | 3/2001 | Hair | | 6,682,540 | B1 | 1/2004 | Sancoff et al. |
| 6,217,611 | B1 | 4/2001 | Klostermeyer | | 6,695,857 | B2 | 2/2004 | Gifford, III et al. |
| 6,221,083 | B1 | 4/2001 | Mayer | | 6,695,859 | B1 | 2/2004 | Golden et al. |
| 6,241,738 | B1 | 6/2001 | Dereume | | 6,695,878 | B2 | 2/2004 | McGuckin et al. |
| 6,241,741 | B1 | 6/2001 | Duhaylongsod et al. | | 6,699,257 | B2 | 3/2004 | Gifford, III et al. |
| 6,248,117 | B1 | 6/2001 | Blatter | | 6,702,826 | B2 | 3/2004 | Liddicoat et al. |
| 6,250,308 | B1 | 6/2001 | Cox | | 6,709,442 | B2 * | 3/2004 | Miller et al. .............. 606/153 |
| 6,254,615 | B1 | 7/2001 | Bolduc et al. | | 6,712,829 | B2 | 3/2004 | Schulze |
| 6,269,819 | B1 | 8/2001 | Oz et al. | | 6,719,768 | B1 | 4/2004 | Cole et al. |
| 6,280,460 | B1 | 8/2001 | Bolduc et al. | | 6,743,243 | B1 | 6/2004 | Roy et al. |
| 6,283,979 | B1 | 9/2001 | Mers et al. | | 6,749,622 | B2 | 6/2004 | McGuckin et al. |
| 6,283,993 | B1 | 9/2001 | Cosgrove et al. | | 6,776,782 | B2 | 8/2004 | Schulze |
| 6,293,955 | B1 | 9/2001 | Houser et al. | | 6,776,784 | B2 | 8/2004 | Ginn |
| 6,296,622 | B1 | 10/2001 | Kurz et al. | | 6,776,785 | B1 | 8/2004 | Yencho et al. |
| 6,296,656 | B1 | 10/2001 | Bolduc et al. | | 6,802,847 | B1 | 10/2004 | Carson et al. |
| 6,306,141 | B1 | 10/2001 | Jervis | | 6,805,708 | B1 | 10/2004 | Yencho et al. |
| 6,332,893 | B1 | 12/2001 | Mortier et al. | | 6,811,555 | B1 | 11/2004 | Willis et al. |
| 6,346,074 | B1 | 2/2002 | Roth | | 6,821,286 | B1 | 11/2004 | Carranza et al. |

| Patent No. | Date | Name |
|---|---|---|
| 6,869,444 B2 | 3/2005 | Gabbay |
| 6,884,250 B2 | 4/2005 | Monassevitch et al. |
| 6,896,684 B2 | 5/2005 | Monassevitch et al. |
| 6,899,718 B2 | 5/2005 | Gifford, III et al. |
| 6,913,607 B2 | 7/2005 | Ainsworth et al. |
| 6,916,327 B2 | 7/2005 | Northrup, III et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,955,679 B1 | 10/2005 | Hendricksen et al. |
| 6,960,221 B2 | 11/2005 | Ho et al. |
| 6,962,596 B2 | 11/2005 | Bolduc et al. |
| 6,966,920 B2 | 11/2005 | Yencho et al. |
| 6,972,023 B2 | 12/2005 | Whayne et al. |
| 6,979,337 B2 | 12/2005 | Kato |
| 6,979,338 B1 | 12/2005 | Loshakove et al. |
| 6,991,636 B2 | 1/2006 | Rose |
| 6,994,713 B2 | 2/2006 | Berg et al. |
| 7,015,002 B2 | 3/2006 | Isobe |
| 7,018,388 B2 | 3/2006 | Yencho et al. |
| 7,022,131 B1 | 4/2006 | Derowe et al. |
| 7,041,112 B2 | 5/2006 | Vargas et al. |
| 7,048,747 B2 | 5/2006 | Arcia et al. |
| 7,056,330 B2 | 6/2006 | Gayton |
| 7,063,711 B1 | 6/2006 | Loshakove et al. |
| 7,070,618 B2 | 7/2006 | Streeter |
| 7,087,064 B1 | 8/2006 | Hyde |
| 7,108,701 B2 | 9/2006 | Evens et al. |
| 7,108,702 B2 | 9/2006 | Yencho et al. |
| 7,112,211 B2 | 9/2006 | Gifford, III et al. |
| 7,128,749 B1 | 10/2006 | Vargas et al. |
| 7,182,769 B2 | 2/2007 | Ainsworth et al. |
| 7,211,095 B2 | 5/2007 | Bachinski et al. |
| 7,220,265 B2 | 5/2007 | Chanduszko et al. |
| 7,220,268 B2 | 5/2007 | Blatter |
| 7,223,273 B2 | 5/2007 | Manzo |
| 7,270,670 B1 | 9/2007 | Yencho |
| 7,291,157 B1 | 11/2007 | Hausen et al. |
| 7,303,569 B2 | 12/2007 | Yencho et al. |
| 7,335,212 B2 * | 2/2008 | Edoga et al. .......... 606/139 |
| 7,338,503 B2 | 3/2008 | Rosenberg et al. |
| 2001/0018592 A1 | 8/2001 | Schaller et al. |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0021858 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0095166 A1 | 7/2002 | Vargas et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Yang et al. |
| 2002/0177859 A1 | 11/2002 | Monassevitch et al. |
| 2003/0065345 A1 | 4/2003 | Weadock |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0114867 A1 | 6/2003 | Bolduc et al. |
| 2003/0125755 A1 | 7/2003 | Schaller et al. |
| 2003/0163143 A1 | 8/2003 | Wakabayashi |
| 2003/0191481 A1 | 10/2003 | Nguyen et al. |
| 2003/0195531 A1 | 10/2003 | Nguyen et al. |
| 2003/0199974 A1 | 10/2003 | Lee et al. |
| 2004/0050393 A1 | 3/2004 | Golden et al. |
| 2004/0068276 A1 | 4/2004 | Golden et al. |
| 2004/0073240 A1 | 4/2004 | Bolduc et al. |
| 2004/0087985 A1 * | 5/2004 | Loshakove et al. .......... 606/153 |
| 2004/0092975 A1 | 5/2004 | Loshakove et al. |
| 2004/0102797 A1 | 5/2004 | Golden et al. |
| 2004/0111099 A1 | 6/2004 | Nguyen et al. |
| 2004/0138685 A1 | 7/2004 | Clague et al. |
| 2004/0172050 A1 | 9/2004 | Bolduc et al. |
| 2004/0176663 A1 | 9/2004 | Edoga |
| 2004/0193259 A1 | 9/2004 | Gabbay |
| 2004/0243154 A1 | 12/2004 | Berg et al. |
| 2004/0249415 A1 | 12/2004 | Vargas et al. |
| 2005/0004582 A1 | 1/2005 | Edoga |
| 2005/0021054 A1 | 1/2005 | Ainsworth et al. |
| 2005/0038454 A1 | 2/2005 | Loshakove et al. |
| 2005/0043708 A1 | 2/2005 | Gleeson et al. |
| 2005/0043749 A1 | 2/2005 | Breton et al. |
| 2005/0065601 A1 | 3/2005 | Lee et al. |
| 2005/0070924 A1 | 3/2005 | Schaller et al. |
| 2005/0075659 A1 | 4/2005 | Realyvasquez et al. |
| 2005/0075667 A1 | 4/2005 | Schaller et al. |
| 2005/0080454 A1 | 4/2005 | Drews |
| 2005/0085834 A1 | 4/2005 | Carranza et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0267572 A1 | 12/2005 | Schoon et al. |
| 2005/0277964 A1 | 12/2005 | Brenneman et al. |
| 2005/0277965 A1 | 12/2005 | Brenneman et al. |
| 2005/0277967 A1 | 12/2005 | Brenneman et al. |
| 2006/0004389 A1 | 1/2006 | Nguyen et al. |
| 2006/0106405 A1 | 5/2006 | Fann et al. |
| 2006/0111704 A1 | 5/2006 | Brenneman et al. |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0118158 A1 | 5/2007 | Deem et al. |
| 2007/0142848 A1 | 6/2007 | Ainsworth et al. |

FOREIGN PATENT DOCUMENTS

| | | |
|---|---|---|
| DE | 2703529 | 1/1977 |
| DE | 3203410 | 5/1981 |
| DE | 3227984 | 2/1984 |
| DE | 3504202 | 8/1985 |
| DE | 4133800 | 10/1991 |
| DE | 4402058 | 4/1995 |
| DE | 19547617 | 9/1997 |
| DE | 19732234 | 1/1999 |
| EP | 0072232 | 2/1983 |
| EP | 0122046 | 3/1983 |
| EP | 0129441 | 12/1984 |
| EP | 0130037 | 1/1985 |
| EP | 0140557 | 5/1985 |
| EP | 0121362 | 9/1987 |
| EP | 0409569 | 1/1991 |
| EP | 0432692 | 6/1991 |
| EP | 0478949 | 8/1991 |
| EP | 0494636 | 7/1992 |
| EP | 0537955 | 4/1993 |
| EP | 0559429 | 9/1993 |
| EP | 0598529 | 5/1994 |
| EP | 0326426 | 12/1994 |
| EP | 0419597 | 12/1994 |
| EP | 0632999 | 1/1995 |
| EP | 0641546 | 3/1995 |
| EP | 0656191 | 6/1995 |
| EP | 0687446 | 12/1995 |
| EP | 0705568 | 4/1996 |
| EP | 0711532 | 5/1996 |
| EP | 0705569 | 10/1996 |
| EP | 0734697 | 10/1996 |
| EP | 0778005 | 6/1997 |
| EP | 0815795 | 1/1998 |
| EP | 915677 | 4/1999 |
| EP | 956825 | 11/1999 |
| EP | 1009293 | 6/2000 |
| EP | 1413256 | 4/2004 |
| EP | 1421909 | 5/2004 |
| EP | 1513459 | 3/2005 |
| GB | 2223410 | 4/1990 |
| JP | 07308322 | 11/1995 |
| JP | 08836544 | 12/1996 |
| JP | 10337291 | 12/1998 |
| RU | 2110222 | 5/1998 |
| SU | 577022 | 10/1977 |
| SU | 1186199 | 10/1985 |

| | | |
|---|---|---|
| SU | 1456109 | 2/1989 |
| SU | 1560133 | 4/1990 |
| WO | 90/06725 | 6/1990 |
| WO | 90/09149 | 8/1990 |
| WO | 90/14795 | 12/1990 |
| WO | 91/07916 | 6/1991 |
| WO | 91/08708 | 6/1991 |
| WO | 91/17712 | 11/1991 |
| WO | 92/05828 | 4/1992 |
| WO | 92/12676 | 8/1992 |
| WO | 92/22041 | 12/1992 |
| WO | 93/01750 | 2/1993 |
| WO | 94/15535 | 7/1994 |
| WO | 94/15537 | 7/1994 |
| WO | 96/00035 | 1/1996 |
| WO | 96/06565 | 3/1996 |
| WO | 96/25886 | 8/1996 |
| WO | 96/38090 | 12/1996 |
| WO | 97/12555 | 4/1997 |
| WO | 97/16122 | 5/1997 |
| WO | 97/27898 | 8/1997 |
| WO | 97/28744 | 8/1997 |
| WO | 97/28745 | 8/1997 |
| WO | 97/31575 | 9/1997 |
| WO | 97/32526 | 9/1997 |
| WO | 97/40754 | 11/1997 |
| WO | 97/42881 | 11/1997 |
| WO | 98/19636 | 5/1998 |
| WO | 98/29040 | 7/1998 |
| WO | 98/30153 | 7/1998 |
| WO | 98/42262 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62406 | 12/1999 |
| WO | 99/62408 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | 00/03759 | 1/2000 |
| WO | 00/15144 | 3/2000 |
| WO | 00/59380 | 10/2000 |
| WO | 00/60995 | 10/2000 |
| WO | 00/64381 | 11/2000 |
| WO | 00/74603 | 12/2000 |
| WO | 01/19292 | 3/2001 |
| WO | 01/26557 | 4/2001 |
| WO | 01/26586 | 4/2001 |
| WO | 01/28432 | 4/2001 |
| WO | 01/30230 | 5/2001 |
| WO | 01/54618 | 8/2001 |
| WO | 01/74254 | 10/2001 |
| WO | 01/95783 | 12/2001 |
| WO | 02/13701 | 2/2002 |
| WO | 02/13702 | 2/2002 |
| WO | 02/30172 | 4/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/026475 | 4/2003 |
| WO | 03/053289 | 7/2003 |
| WO | 03/063691 | 8/2003 |
| WO | 03/088875 | 10/2003 |
| WO | 03/101311 | 12/2003 |
| WO | 2004/008936 | 1/2004 |
| WO | 2005/011468 | 2/2005 |
| WO | 2005/018683 | 3/2005 |
| WO | 2005/058170 | 6/2005 |
| WO | 2005/122919 | 12/2005 |
| WO | 2006/057920 | 6/2006 |
| WO | 2006/108050 | 10/2006 |
| WO | 2008/086287 | 7/2008 |

OTHER PUBLICATIONS

Approach to Treat Mitral Regurgitation due to Severe Myxomatous Disease: Surgical Technique, European Journal of Cardiothoracic Surgery, vol. 17, 2000, pp. 201-205.

Chitwood Jr., Mitral Valve Repair: Ischemic, Mastery of Cardiothoracic Surgery, Lippencott-Raven Publishers, 1998, pp. 309-321.

Emery, et al., "Suture Techniques for MIDCAB Surgery," Chapter 12 in *Techniques for Minimally Invasive Direct Coronary Artery Bypass (MIDCAB) Surgery*. R.W. Emery ed., Hanley & Belfus, Inc.: Philadelphia, PA, 1997, pp. 87-91.

Grondin, et al., Carpentier's Annulus and De Vega's Annuloplasty, Nov. 1975, pp. 852-861.

Holper, et al., Surgery For Tricuspid Insufficiency: Long Term Follow-Up After De Vega Annuloplasty, Sep. 9, 1992.

Maisano, et al. The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.

Rabago, The New De Vega Technique in Tricuspid Annuloplasty, pp. 231-238, Mar. 1980.

Rivera, et al., Carpentier's Flexible Ring Versus De Vega's Annuloplasty, Feb. 1985, pp. 196-203.

Wei, et al., De Vega's Semicircular Annuloplasty For Tricuspid Valve Regurgitation, Jun. 2, 1992, pp. 482-485.

Wylie, et al., Manual of Vascular Surgery, R. H. Egdahl ed. Spring-Verlag: New York, vol. I & II, 1986, Table of Contents only (10 pages).

Wylie, et al., Manual of Vascular Surgery, Springer-Verlag New York, 1980, Table of Contents only (3 pages).

Yun, et al. Mitral Valve Replacement, Mastery of Cardiothoracic Surgery, Lippencott-Raven Publishers, pp. 329-341, 1998.

International Search Report PCT/US98/00462, 1998.
International Search Report PCT/US98/00795, 1998.
International Search Report PCT/US98/14211, 1998.
International Search Report PCT/US99/12563, 1999.
International Search Report PCT/US99/12566, 1999.
International Search Report PCT/US00/09092, 2000.
International Search Report PCT/US01/10501, 2001.
International Search Report PCT/US01/31709, 2001.
International Search Report PCT/US01/42653, 2001.
International Search Report PCT/US02/10865, 2002.
International Search Report PCT/US02/10866, 2002.
International Search Report PCT/US02/14261, 2002.
International Search Report PCT/US03/12073, 2003.
International Preliminary Examination Report PCT/US98/00462, 1998.
International Preliminary Examination Report PCT/US98/00795, 1998.
International Preliminary Examination Report PCT/US99/12566, 1999.
International Preliminary Examination Report PCT/US00/09092, 2000.
International Preliminary Examination Report PCT/US01/31709, 2001.
International Preliminary Examination Report PCT/US01/42653, 2001.
International Preliminary Examination Report PCT/US02/14261, 2002.
International Preliminary Examination Report PCT/US02/10865, 2002.
International Preliminary Examination Report PCT/US02/10866, 2002.
International Preliminary Examination Report PCT/US03/12073, 2003.

Written Opinion PCT/US99/12563, 1999.
Written Opinion PCT/US99/12566, 1999.
Written Opinion PCT/US00/09092, 2001.
Written Opinion PCT/US01/10501, 2001.
Written Opinion PCT/US01/31709, 2001.
Written Opinion PCT/US02/10866, 2002.
Written Opinion PCT/US02/14261, 2002.
Written Opinion PCT/US03/12073, 2003.
International Preliminary Report on Patentability PCT/US2004/023728, 2004.
US 6,503,260, 01/2003, Schaller et al. (withdrawn)

* cited by examiner

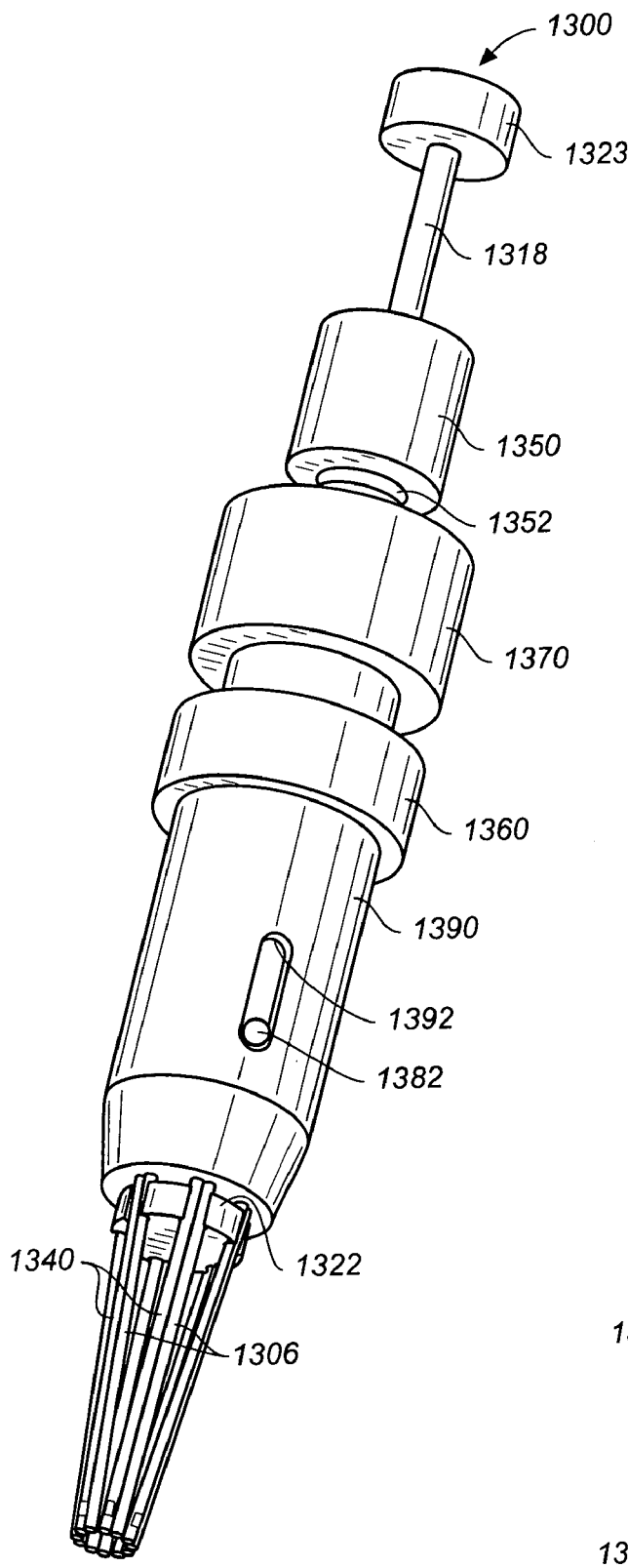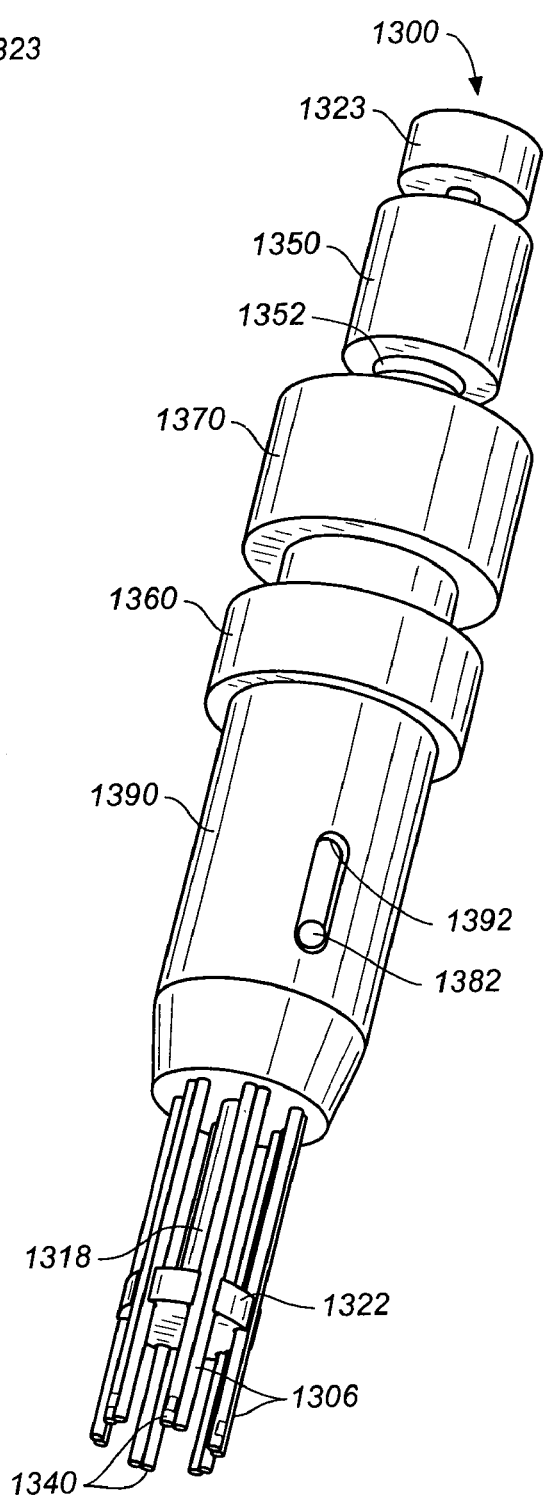
FIG._1A  FIG._1B

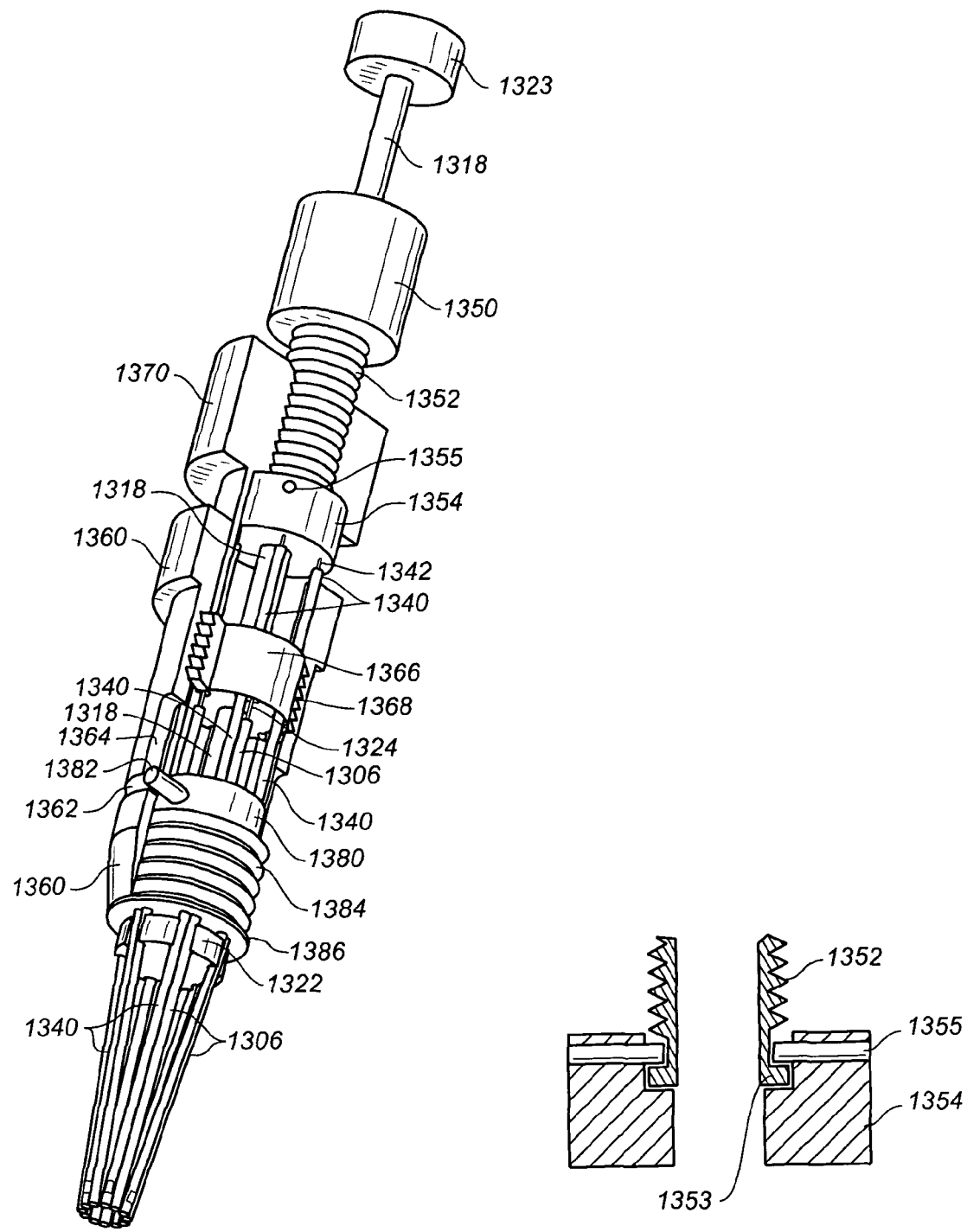
FIG._2A  FIG._2B

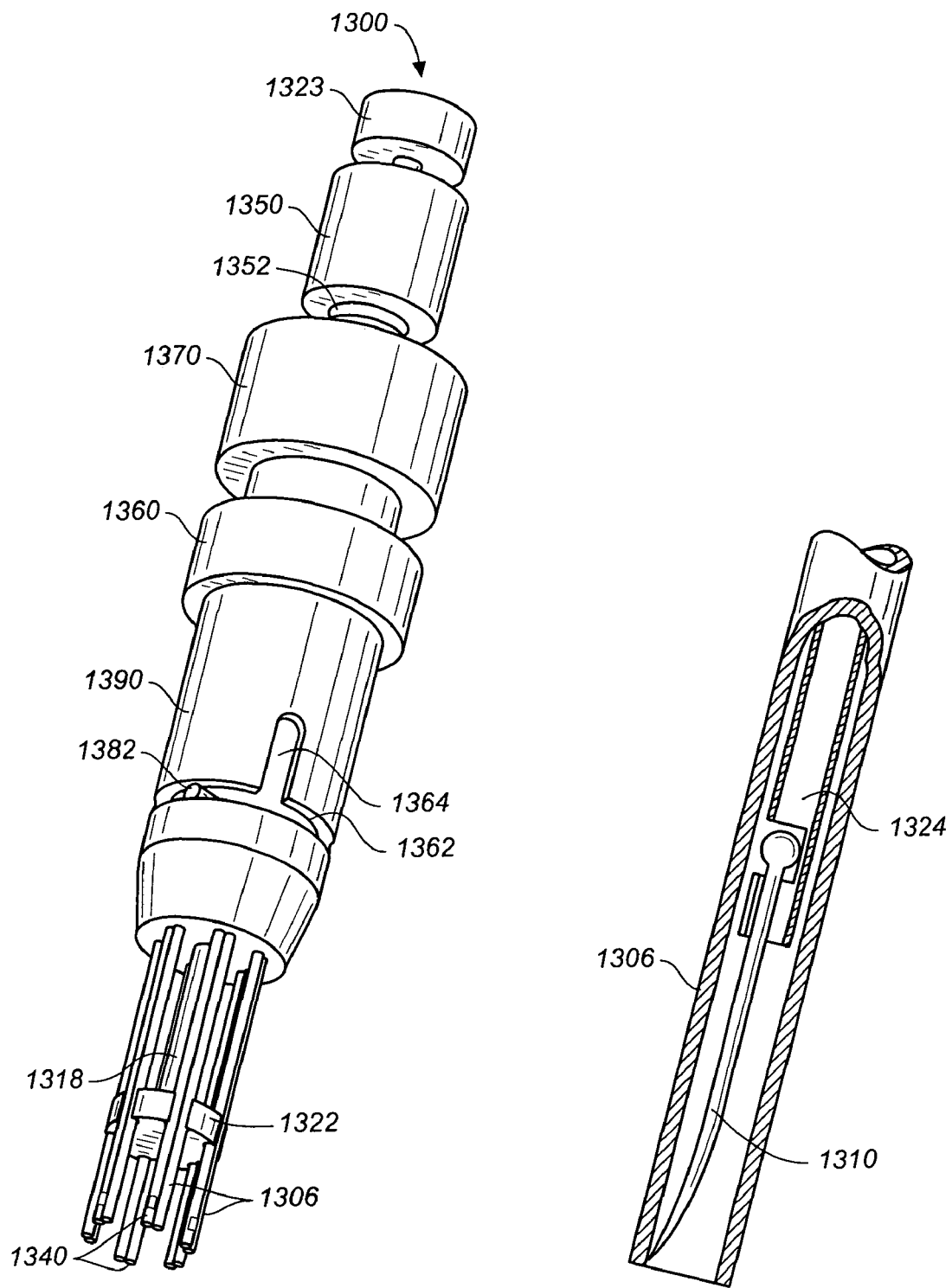
FIG._3A   FIG._3B

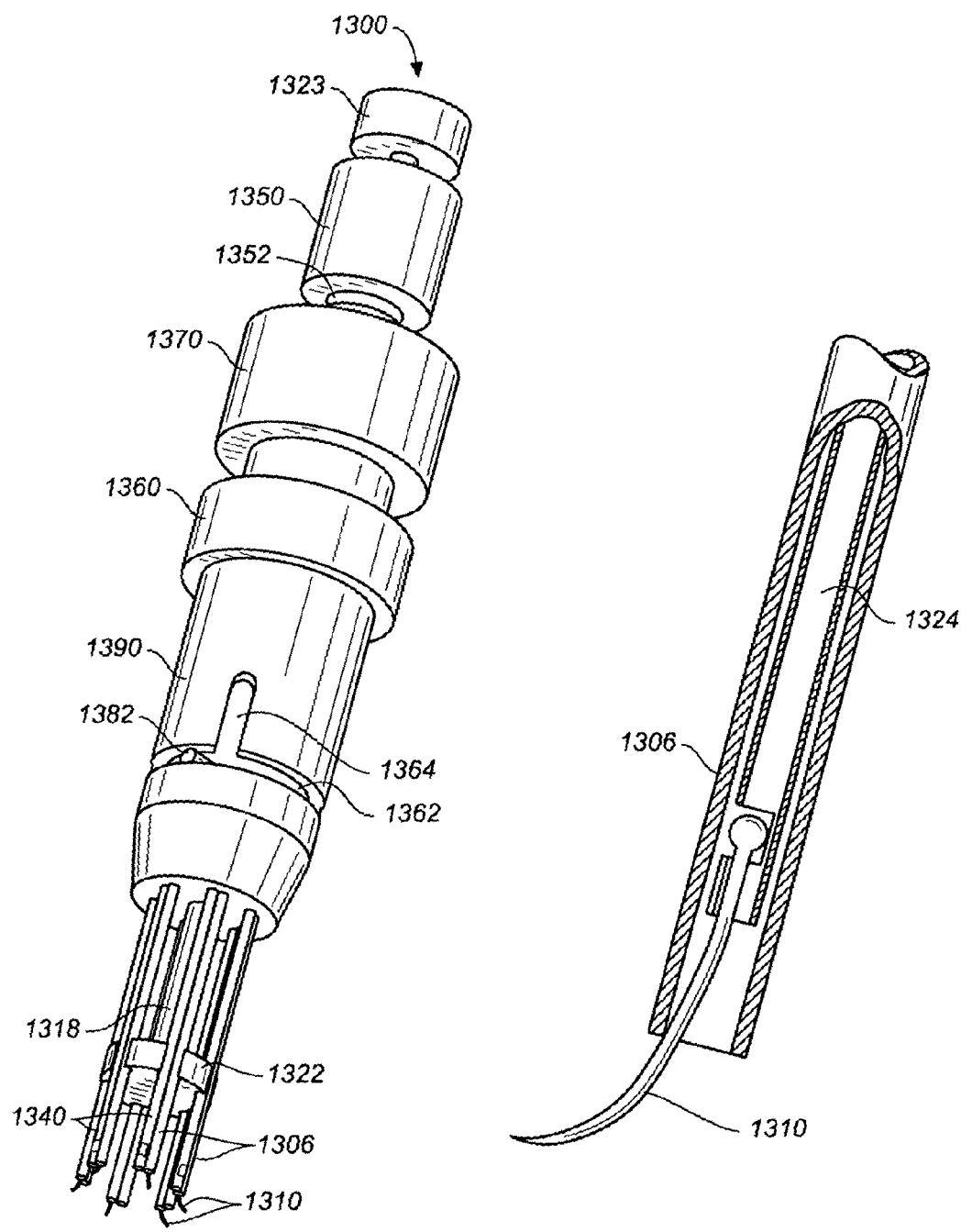
FIG._4A   FIG._4B

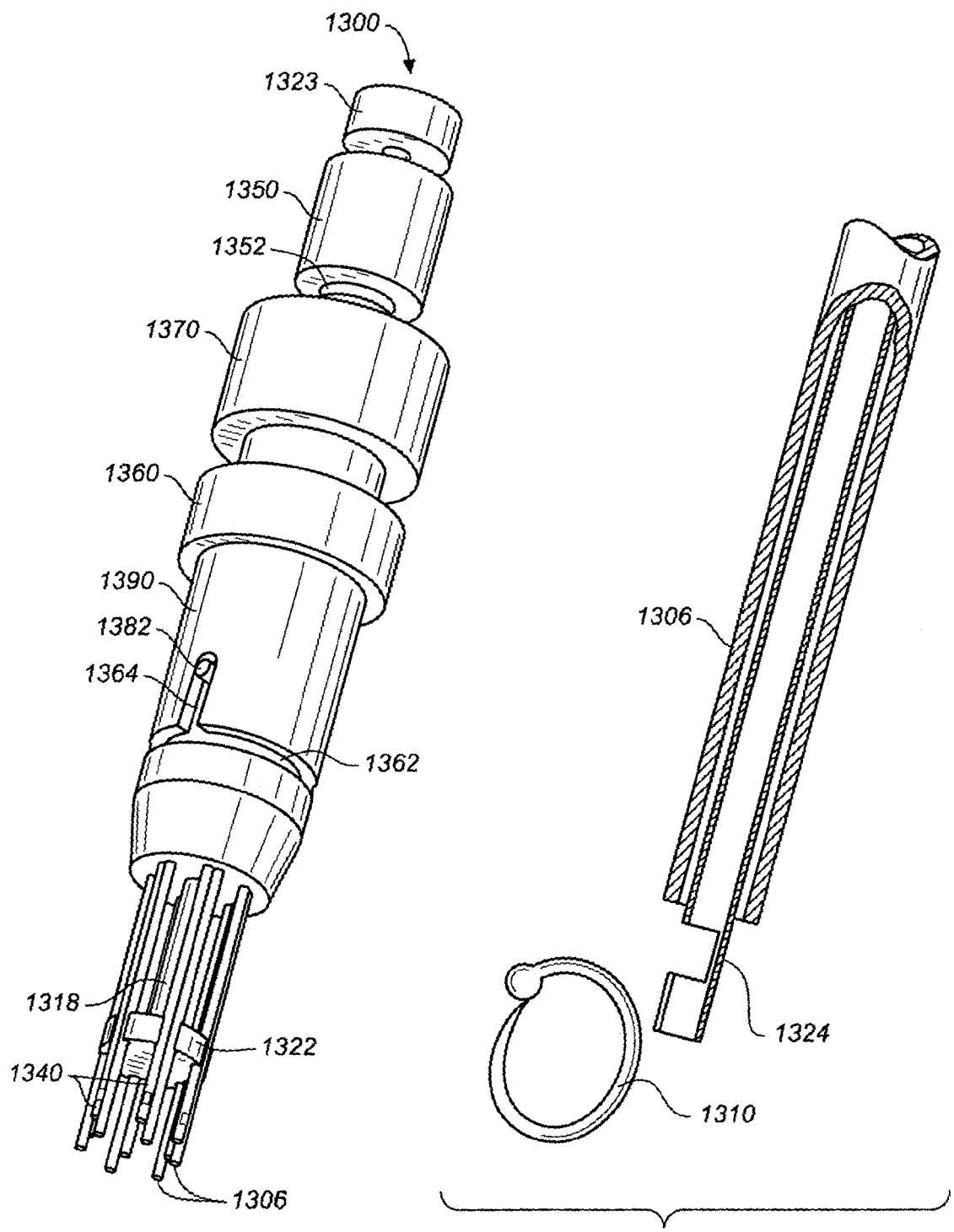

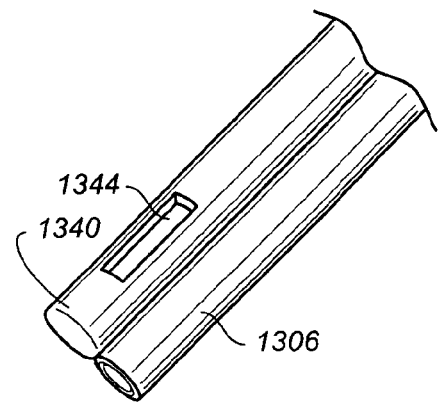
FIG._6A
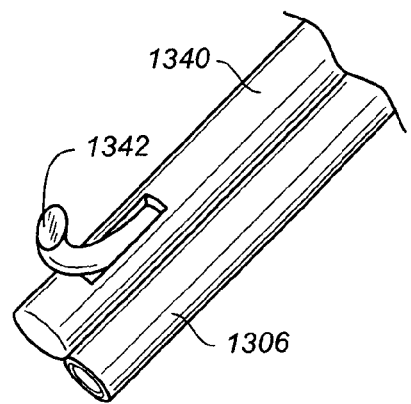
FIG._6B
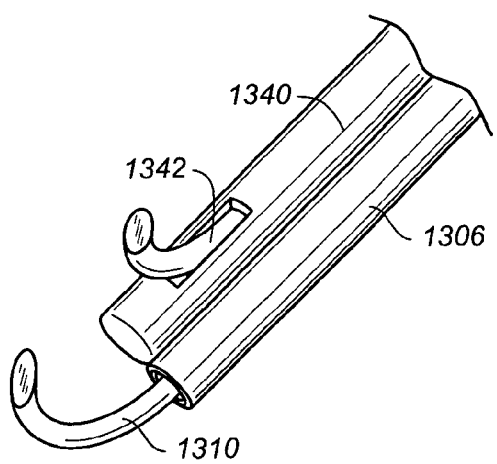
FIG._6C
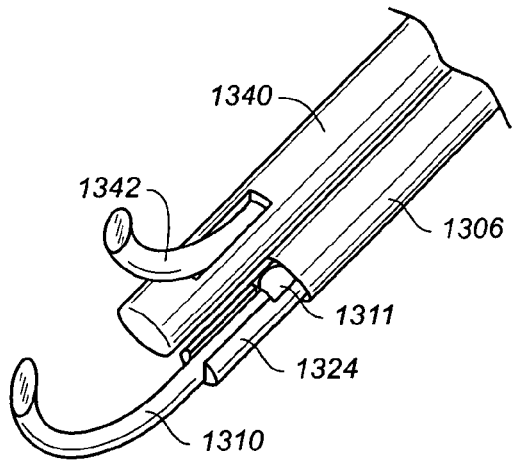
FIG._6D

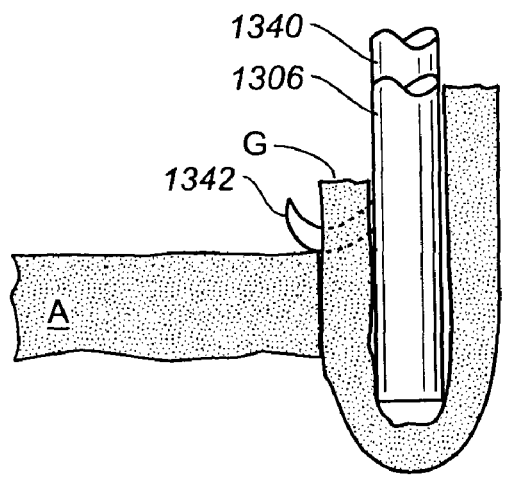
FIG._7A
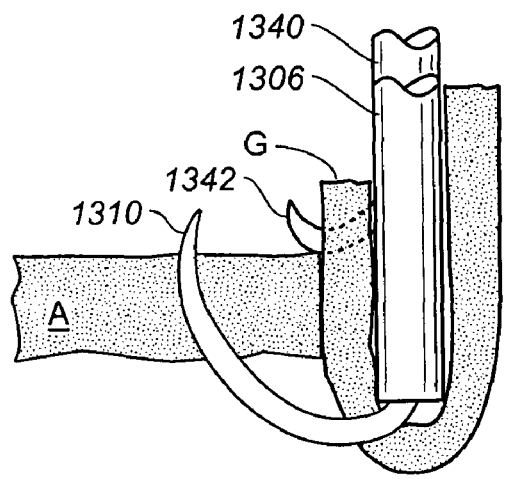
FIG._7B
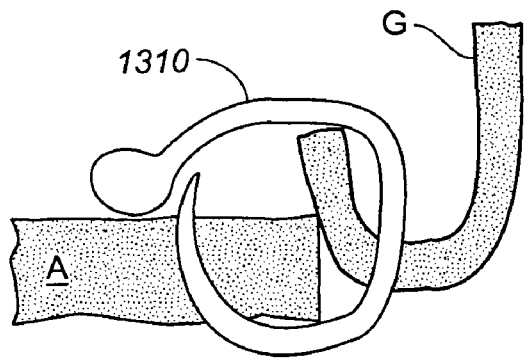
FIG._7C

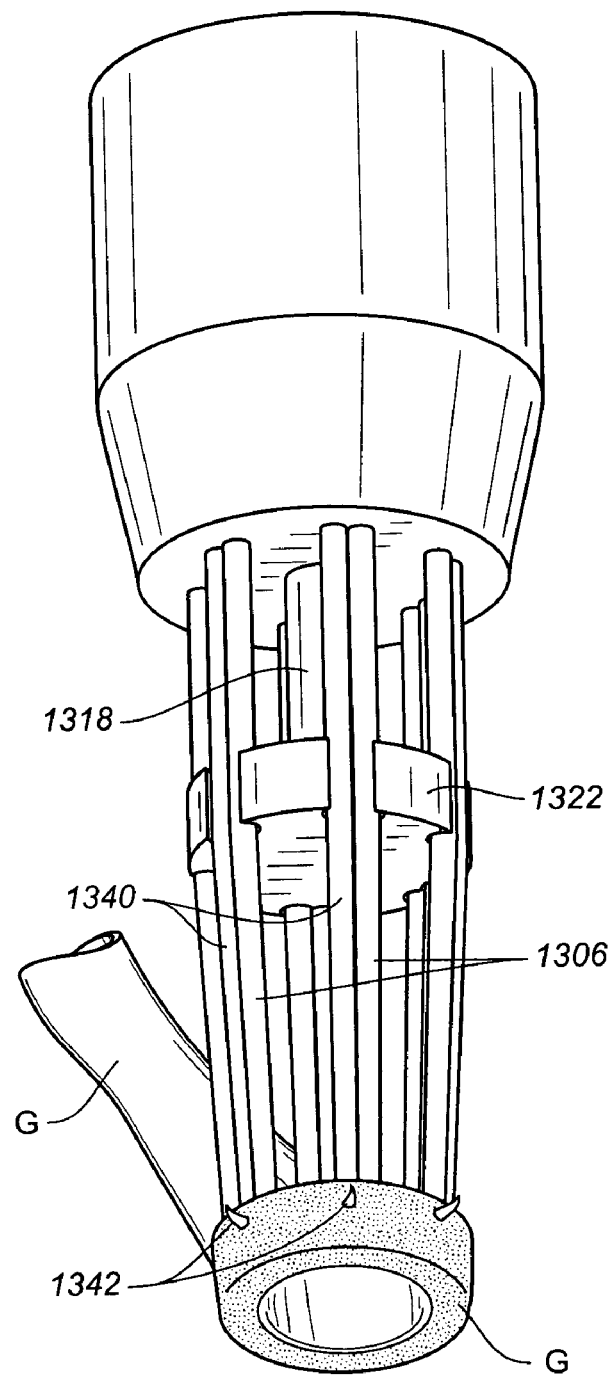
FIG._8A
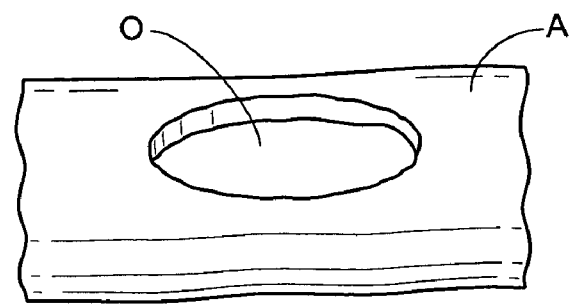

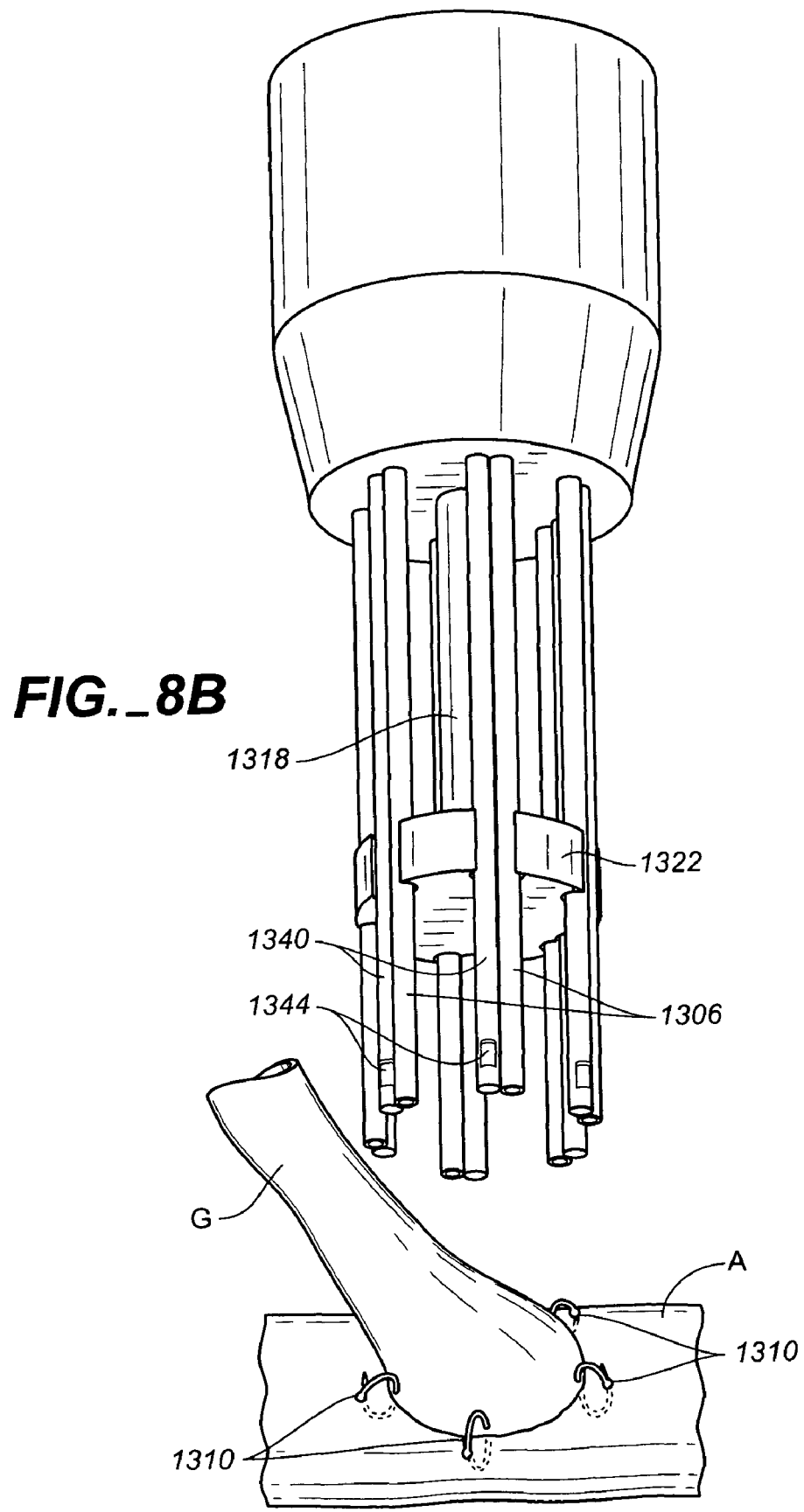
FIG._8B

SURGICAL CONNECTION APPARATUS AND METHODS

FIELD OF THE INVENTION

This invention relates to apparatus and methods for surgically joining structures. More particularly, the invention can involve anastomosing tubular structures and can be used, for example, in a proximal anastomosis.

BACKGROUND OF THE INVENTION

The occlusion of the arteries can lead to insufficient blood flow resulting in discomfort and risks of angina and ischemia. Significant blockage of blood flow in the coronary artery can result in damage to the myocardial tissue or death of the patient. In most cases, occlusion of the artery results from progressive long term deposits of plaque along the artery wall. While such deposits may be concentrated and occlude the artery at a particular site, the deposits are most certainly present throughout the arteries and the vascular system.

Coronary artery bypass graft (CABG) surgery is a surgical procedure performed in severe cases of coronary blockages. CABG procedures involve anastomosing an artery to a vascular graft which restores the flow of blood by establishing another pathway around the occluded vasculature. During coronary artery bypass graft surgery, a vein or other conduit can be attached proximally to the patient's aorta. The other end is attached to the blocked artery, downstream from the obstruction, thus bypassing the coronary occlusion. CABG procedures can be done by placing the patient on a heart-lung machine and stopping the heart from beating or they can be done on a beating heart without a heart lung machine. One problem encountered in either CABG procedure is the need to perform the procedure, while simultaneously maintaining sufficient function of the patient's circulatory system.

In the case where a CABG procedure involves arresting the heart so that blood flow is diverted from the vessel to be anastomosed, the patient's blood circulation is maintained by a cardiopulmonary bypass (CPB). This bypass is accomplished by diverting the blood flow at selected arterial locations. The blood is diverted to the bypass system for release of carbon dioxide and subsequent oxygenation. Then, the blood is returned to the patient via a pump. Examples of these procedures are found in U.S. Patents: U.S. Pat. No. 5,799,661 to Boyd, et al. which discloses a device and method for performing CABG surgery for multi-vessel coronary artery disease through port-access or closed-chest thorascopic methods; and U.S. Pat. No. 5,452,733 to Sterman, et al. which discusses performing grafts with an efficacy equal to or greater than conventional open surgical bypass techniques.

Although the beating heart CABG procedure eliminates the need for CPB, it has required diverting blood flow for a proximal anastomosis, such as one which attaches graft material (e.g., a graft vessel) to the ascending aorta. To attach the graft to the aorta in a beating heart situation, surgeons have typically used a "side-biting clamp" that isolates the aortic region where the anastomosis will be performed. This allows the surgeon to create the anastomosis without the site being exposed to the high-pressure blood flow of the normal aorta.

Among the drawbacks associated with aortic clamping are an increased chance of trauma to the arteries caused by ligatures at the clamped site and the possible dislodging of plaque within the clamped vessel wall. As mentioned above, the arterial bypass may be required due to the deposits of plaque which have occluded the vessel. However, the plaque is typically present throughout the artery and is not limited to the occluded location. Clamping the artery creates a risk of plaque being released into the blood stream. This release of plaque has the potential of causing a stroke, occlusion of a smaller peripheral vessel, or other vascular trauma. In a beating heart procedure, full clamping (i.e., cross clamping) of the aorta for graft attachment at the proximal anastomosis is not feasible. Therefore a side biting clamp is used to clamp off only a portion of the cross-section of the aorta, where the proximal anastomosis is performed. This type of clamping procedure poses the same risks described above with regard to cross clamping, e.g., the risk of release of plaque and resultant cause of a stroke, occlusion of a smaller peripheral vessel, or other vascular trauma.

Other attempts to address the problem related to blood flow diversion include diverting the blood by placing a balloon catheter within the aorta, such as described in U.S. Pat. No. 5,868,702 to Stevens, et al., for example. Drawbacks of using a balloon catheter in creating a seal to divert blood flow include the possibility of disturbing plaque deposits and creating particles in the blood stream, the chance that the balloon catheter may move within the aorta disrupting the seal and resulting in blood loss, and trauma to aortic tissue caused by the pressure needed to create the seal.

There remains some concern in the surgical community that neurological defects and strokes are associated with the use of heart-lung machines, side-biting clamps, and balloon occlusion devices.

PCT Patent Application No. PCT/US98/10245, to Cardio Medical Solutions and to Nobles, et al., which published under Publication No. WO 98/52475, attempts to address problems associated with diverting blood flow. Nobles, et al. provides a method and device for creating an area of hemostasis within a blood vessel without interrupting the flow of blood through the vessel which eliminates the need to clamp the vessel. However, the Nobles, et al. device requires the withdrawal of the hemostasis device prior to obtaining a tight seal between the graft and vessel. Therefore, since the area of hemostasis is lost upon the retrieval of the hemostasis device, the artery is open and blood is lost until the sutures are tightened.

Yet another problem related to CABG procedures lies in the procedure of suturing the vessels to create a tight seal. To ensure the integrity and patency of the anastomosis, the graft and vessel to be joined thereto must be precisely aligned with respect to each other. If one of the tissues is affixed too close to its edge, the suture can tear through the tissue and impair both the tissue and the anastomosis. Another problem is that, even after proper alignment of the tissue, it is difficult and time consuming to pass the needle through the tissues, form the knot with the suture material, and ensure that the suture material does not become entangled. These difficulties are exacerbated by the small size of the artery and graft. Another factor contributing to the difficulty of the CABG procedure is the limited time available to complete the procedure. The surgeon must complete the graft in as little time possible due to the absence of blood flowing through the artery. If blood flow is not promptly restored, sometimes in as little as 30 minutes, the tissues the artery supplies may experience significant damage or necrosis. As mentioned above, surgeons are under pressure to reduce the cross-clamp time, yet, an incomplete suture may result in a leak in the tissue approximation between the vessel and graft. Moreover, the tissue approximation must be smooth and open. Hence, the suture cannot be hastily performed.

Additionally, the difficulty of suturing a graft to an artery using minimally invasive surgical techniques, where the surgeon uses ports to access the internal organs to perform the procedure, has effectively prevented the safe use of complicated suturing technology in cardiovascular surgical procedures. Accordingly, many procedures are performed invasively and require a sternotomy, an opening of the sternum. As a result, the recovery times for patients is significantly increased. U.S. Pat. No. 5,868,763 to Spence, et al. attempts to circumvent the suturing process by attaching the vessels to a cuff device. Spence, et al. utilizes a passageway for continued blood flow so there is no clamping of the artery.

Arcia, et al., in U.S. Pat. No. 6,358,258, describes systems and methods for performing anastomosis or attachments of body ducts, which are asserted to simplify suture delivery in both stopped heart and beating heart procedures and to be suitable for use in a minimally invasive environment using percutaneous ports, or with retractor systems or in a generally open surgery environment. Bolduc, et al., in U.S. Pat. No. 6,461,365, describes surgical clips and methods of tissue approximation and attachment which are asserted as being useful in open surgical procedures as well as endoscopic, laproscopic, thoracoscopic and other minimally-invasive procedures.

Houser, et al., in U.S. Pat. No. 5,989,276, discloses various devices and techniques for performing bypass, one of which includes a device which can be intralumenally originated. Various other clamping arrangements are provided for securing a graft to a vessel without the use of sutures or other fasteners.

In PCT Application No. PCT/GB01/04666, to Anson Medical Limited and to Hopkinson, et al., and which published under Publication No. WO 02/34143, apparatus is described for carrying out an anastomosis by sealing an arteriotomy and connecting a graft to the artery with the seal in place (see the Abstract). The apparatus includes means for sealing the hole and means for locating the graft on the outside of the wall of the artery. Once the graft is completely connected, the seal can be removed from the artery through the bore of the graft. Means may be provided for clamping the graft and seal in place while the graft is being connected to free both of the surgeon's hands for the connection operation.

The problems discussed above can be exacerbated in those cases where multiple attachments or multiple anastomosis procedures are required. In those cases where multiple bypass procedures are performed, the patient will naturally be subject to increased risks as multiple grafts must be sutured to perform the bypass. Therefore, there is a need to improve and simplify surgical connection procedures such as anastomosis procedures.

SUMMARY OF THE INVENTION

The present invention involves improvements in surgical connection apparatus and methods. According to one embodiment of the invetnion, surgical connection apparatus comprises a support structure; a plurality clips (e.g., self-closing clips) releasably coupled to the support structure; and a plurality of barbs coupled to the support structure and being separate from the clips, which are ejectable from the support structure independently of the barbs. The barb and clip arrangement can improve clip positioning uniformity and/or graft or prosthesis attachment consistency and/or efficacy. It also may advantageously reduce procedure time.

The clips also can be arranged for simultaneous ejection from the support structure, which can further reduce procedure time and improve graft attachment consistency and/or efficacy.

According to another embodiment, surgical connection apparatus comprises a support structure forming a first plurality of paths and a second plurality of paths; a plurality of clips, each clip being slidably disposed in one path of the first plurality of paths; and a plurality of barbs, each slidably disposed in one path of the second plurality of paths.

According to another embodiment, surgical connection apparatus for connecting a first structure to a second structure comprises a support structure, a plurality of barbs coupled to the support structure, a plurality of clips slidably coupled to the support structure and unattached to the barbs; means for moving the barbs; and means for ejecting the clips from the support structure.

According to another embodiment, surgical connection apparatus for connecting a first structure to a second structure comprises a support structure, a plurality of barbs coupled to the support structure, a plurality of clips slidably coupled to the support structure and unattached to the barbs; and means for simultaneously ejecting the plurality of clips.

According to another embodiment, surgical connection apparatus for connecting a first structure to a second structure comprises a support structure, a plurality of barbs, each coupled to the support structure and having a distal end portion, a plurality of clips slidably coupled to the support structure, means for moving the barbs between a first position where the distal end portions are inside the support structure to a second position where the distal end portions extend from the support structure; and means for ejecting the clips from the support structure.

According to another embodiment, a method of performing an anastomosis comprises everting a tubular graft structure over a support structure and passing a plurality of barbs from the support structure into the graft to secure the graft to the support structure; introducing the everted portion of the tubular graft structure into an opening formed in a second tubular structure; and simultaneously passing a plurality of clips through the tubular graft structure and second tubular structure to secure the graft and second tubular structures together.

According to another embodiment, a method of surgically connecting structures in patient comprises placing a first structure on a support structure and passing a plurality of barbs from the support structure into the first structure to secure the first structure to the support structure; placing the support structure adjacent a second structure in a patient; and simultaneously passing a plurality of clips through the first and second structures to secure the first and second structures together.

The above is a brief description of some deficiencies in the prior art and. advantages of the present invention. Other features, advantages, and embodiments of the invention will be apparent to those skilled in the art from the following description, accompanying drawings, wherein, for purposes of illustration only, specific forms of the invention are set forth in detail.

BRIEF DESCRIPTION OF THE DRAWINGS

FIG. 1A is a perspective view of an anastomosis device in accordance with the principles of the present invention and shown in a first state;

FIG. 1B illustrates the embodiment of FIG. 1A in a second state;

FIG. 2A is a partial longitudinal section of the device of FIG. 1A;

FIG. 2B is a longitudinal section of a portion of the device shown in FIG. 2A;

FIG. 3A shows the device of 1A with the clip actuator assembly position prior to clip deployment;

FIG. 3B is a sectional view of a clip delivery tube of FIG. 3A prior to clip deployment;

FIG. 4A shows the device of FIG. 1A with the clip actuator assembly manipulated to partially deploy a clip;

FIG. 4B is a sectional view of a clip delivery tube of FIG. 4A with a clip partially deployed;

FIG. 5A shows the device of FIG. 1A with the clip actuator assembly manipulated for full clip deployment;

FIG. 5B is a sectional view of a clip delivery tube of FIG. 4A with a clip fully deployed;

FIGS. 6A-D illustrate a distal end portion of one of the tube pairs of the device of FIG. 1A where FIG. 6A shows the distal end portion before barb or clip deployment, FIG. 6B shows the distal end portion with a barb deployed, FIG. 6C shows the distal end portion with a barb deployed and a clip partially deployed, and FIG. 6D shows the distal end portion with a barb deployed and the proximal end of the clip positioned for full deployment;

FIG. 7A illustrates a graft everted over a tube pair and a barb extended to engage the graft;

FIG. 7B illustrates the graft and barb combination of FIG. 7A positioned in a target structure with a clip extended or partially deployed to engage the graft and target structure;

7C illustrates full deployment of the clip illustrated in FIG. 7B and the barb removed;

FIG. 8A illustrates a graft everted over the distal end portion of the device of FIG. 1A prior to placement in a vessel opening; and FIG. 8B illustrates a completed anastomosis and removal of the anastomosis device illustrated in FIG. 1A.

DETAILED DESCRIPTION OF THE INVENTION

Before the present invention is described, it is to be understood that this invention is not limited to particular embodiments or examples described, as such may, of course, vary. Further, when referring to the drawings, like numerals indicate like elements.

The devices, systems, and methods described herein generally can be used to surgically connect structures in a patient. They can be used to connect or anastomose tubular structures or conduits together. The tubular structures can be vascular or nonvascular structures. The illustrative embodiments will be described in connection with coronary artery bypass grafting procedures during which a vascular conduit or graft structure, such as a vein (e.g., a saphenous vein), artery (e.g., an internal mammary artery), or an artificial conduit or graft structure, is anastomosed to an aorta, the example target structure. It should be understood, however, that the invention can be used in other applications not specifically described herein. For example, the devices also can be used to anastomose internal mammary arteries to coronary arteries, and saphenous veins to coronary, femoral or popliteal arteries. As noted above, the devices described herein also can be used to connect other body lumens including nonvascular lumens, which can include, but are not intended to be limited to, the bile duct, the urethra, the urinary bladder, intestines, esophagus, stomach, and bowel.

Referring to FIG. 1A, one embodiment of surgical connection apparatus in accordance with the principles of the present invention is illustrated and generally designated with reference numeral 1300. In the illustrative example, apparatus 1300 is constructed for delivering piercing members or surgical clips 1310, which include ball shaped proximal ends 1311, sharp distal ends, and a loop shaped memory set shape or configuration (see e.g., FIGS. 3B, 5B and 6D), which although shown as an overlapping loop, can be non-overlapping or otherwise shaped differently than that shown. Accordingly, piercing member or clip 1310 is a self-closing closing clip and can be nitinol wire and provided with the desired memory set configuration to exhibit pseudoelastic (supereastic) behavior. In other words, at least a portion of the shape memory alloy is converted from its austenitic phase to its martensitic phase when the wire is in its deformed configuration. As the stress is removed, the material undergoes a martensitic to austenitic conversion and springs back to its original undeformed configuration.

The shape memory alloy can be selected with a transformation temperature suitable for use with a stopped heart condition where cold cardioplegia has been injected for temporary paralysis of the heart tissue (e.g., temperatures as low as 8-10 degrees Celsius).

The cross-sectional diameter of the wire and length of the wire will vary depending on the specific application. The diameter of the wire may be, for example, between 0.001 and 0.015 inch. For coronary bypass applications, the diameter is preferably between 0.001 and 0.008 inch with a diameter of the wire loop in its closed configuration being between 0.0125 and 0.0875 inch. The wire may be formed in a loop shape by first wrapping the wire onto a mandrel and heat treating the wire at approximately 400-500 degrees Celsius for approximately 5 to 30 minutes. The wire is then air quenched at room temperature.

It is to be understood that the shape memory alloy may also be heat activated, or a combination of heat activation and pseudoelastic properties may be used as is well known by those skilled in the art.

Referring to FIGS. 1A and 1B, anastomosis device or apparatus 1300 generally includes a support structure for supporting the clips and can include an actuator for simultaneously deploying or ejecting the piercing members or clips. In the exemplary embodiment, the support structure comprises a plurality of piercing member or clip deploying or ejecting arms 1306, which form paths for the clips to move and be ejected therefrom. The arms can be tubular members and can comprise hypotubes. In the illustrative example, the support structure can further include barb supports, which also can be in the form of path forming arms. These arms also can be tubular members and can comprise hypotubes. As shown in the exemplary embodiment of FIGS. 1A and 1B, the arms are arranged to form a plurality of arm pairs, each arm pair including a clip carrying arm 1306 in which clip 1310 is slidably mounted or disposed and a barb carrying arm 1340 in which barb 1342 is slidably mounted or disposed (FIGS. 6A-D). Although six arm pairs are shown, generally five to twelve arm pairs typically may be used depending on the application.

Arms 1306, which have an open distal end, and arms 1340, which have a rounded closed distal end, are arranged in spring body or spring support cylinder 1380 (FIG. 2A) so as to converge toward their distal ends as shown in FIGS. 1A and 2A. A spreader or slide 1322, which can be generally in the form of a disc, can be used to radially expand the arm pairs from this configuration. One side of spreader or slide 1322 can be secured to shaft 1318, which can have a knob such as knob 1323 secured to a proximal end thereof. Spreader or slide 1322 has a plurality of circumferentially spaced longitudinal openings or grooves in which the barb-clip arm pairs are slidably disposed. As shown, each barb-clip arm pair is slidably diposed in a spreader opening or groove. When slide 1322 is in a proximal position as shown in FIG. 1A, arms 1306 and 1340 are in their converging configuration. As knob 1323 is moved distally, spreader or slide 1322 moves distally and expands arms 1306 and 1340 radially outward as shown in FIG. 1B.

Surgical connection or anastomosis device 1300 can include one or more mechanisms for deploying the barbs and/or clips. It can include an actuator assembly for simultaneously deploying the barbs and an actuator assembly for simultaneously deploying the clips. In the illustrative example, one actuator assembly for simultaneously deploying barbs includes an actuator knob 1350 and one actuator assembly for simultaneously deploying clips includes an actuator knob 1360. Body member or knob 1370 can be provided for the surgeon to hold while manipulating actuator knobs and a cover sleeve 1390, having a longitudinal slot 1392 formed therein, can be provided to cover the clip actuator assembly.

Referring to the illustrative example in FIG. 2A, the barb actuator assembly can generally include knob 1350, threaded member 1352, and cylinder or plunger 1354, which is secured or keyed to shaft 1318 to prevent relative rotation therebetween. Knob 1350 surrounds shaft 1318 and threaded member 1352 is fixedly secured to knob 1350. The threads on threaded member 1352 are configured to engage the inner threaded portion of knob 1370 so that knob 1370 can be maintained in a stationary position as member 1352 is rotated. Threaded member 1352 is coupled to cylinder 1354 to convert the rotational motion of member 1352 to linear motion in cylinder or plunger 1354 so that cylinder 1354 moves distally or in an axial direction. One example mechanism is shown in FIG. 2B where threaded member 1352 has a flange 1353 at its distal end that is free to rotate in an annular groove formed in cylinder 1354. Retaining pins 1355 retain flange 1353 in the annular groove. As threaded member 1352 rotates and moves cylinder or plunger 1354 distally, cylinder 1354 pushes the proximal ends of barbs 1342, which are glued or otherwise secured thereto. This extends the distal ends of the barbs through windows 1344 and moves the distal ends of the barbs from a position inside arms 1340 to a position where they extend from arms 1340 (see e.g., FIGS. 6A and 6B).

The barbs or piercing members can be made from shape memory material such as nitinol and the distal ends of the barbs provided with a desired memory set shape such as the illustrated hook shape. Procedures similar to those described above can be used to set the shape. When the distal end of the barb exits tube 1340 and is no longer biased toward a generally straight configuration by tube 1340, it exhibits its pseudoelastic (superelastic) behavior and assumes its memory set hook shape as shown for example in FIG. 6B.

One embodiment of a clip deployment or ejection actuator assembly also is shown in FIG. 2A. In this embodiment, the clip deployment or ejection actuator assembly generally includes knob 1360 and cylinder or plunger 1366, which is secured or keyed to shaft 1318. Since shaft 1318 is fixedly secured to spreader 1322, shaft 1318 and cylinder 1366 are prevented from rotation relative to spreader 1322. Further, barb tubes 1340 extend longitudinally through cylinder or plunger 1366 and prevent cylinder or plunger 1366 from rotating relative thereto.

Cylinder 1366 is shown in partial section in FIG. 2A and includes a threaded outer surface 1368 that cooperates with threaded inner surface of knob 1360. These threaded portions are configured so that cylinder 1366 moves distally when knob 1360 is rotated in one direction. As cylinder 1366 moves distally, it pushes pusher arms 1324, which can be secured thereto. Each pusher arm can have an inner diameter less than the diameter of the ball shaped proximal end 1311 of a clip so that the pusher arms begin to eject or deploy clips 1310 (see e.g., FIGS. 4A, 4B and 6C).

The clip deployment actuator mechanism also can include a mechanism to retract the clip tubes 1306 when the clips are partially deployed and engaged with the target and/or graft structure. One embodiment of a mechanism to retract the clip tubes generally includes compression coil or spring support cylinder 1380, which includes a pin 1382 radially extending therefrom, coil spring 1384, which is coiled around cylinder 1380, and retaining plate 1386. In this embodiment, knob 1360 is provided with a circumferential opening 1362, which can extend less than or up to 360°, and a longitudinal opening 1364 extending therefrom. Spring 1384 is compressed between pin 1382 and plate 1386 when pin 1382 is not aligned with longitudinal opening 1364. However, spring 1384 is allowed to expand when pin 1382 is aligned with longitudinal opening 1364. In FIG. 2A, the pin is shown at the moment it is aligned with longitudinal opening 1364 and just prior to moving proximally therealong as spring 1384 is allowed to expand. Clip arms 1306 extend longitudinally through spring cylinder 1380 and are fixedly secured thereto by gluing, swaging or any other suitable means. In this manner, clip arms 1306 move with cylinder 1380. In contrast, barb arms 1340 are slidably disposed in longitudinal bores formed in spring cylinder 1380. Thus, when cylinder 1380 is retracted or moved proximally relative to spreader 1322, for example, the barb arms need not move therewith. The operation of the clip arm or tube mechanism is further illustrated in FIGS. 3-5.

Referring FIG. 3A, the clip actuator assembly position prior to clip deployment with pin 1382 spaced from longitudinal opening 1364 and compressing spring 1384 against plate 1386. Each clip is ready for deployment as shown in FIG. 3B with tubular arm 1306 restraining the self-closing clip 1310 in an open configuration or biasing the clip away from its memory set closed configuration. In FIG. 3B, clip 1310 is shown biased toward a generally straight configuration. After knob 1360 is partially rotated, clip 1310 is partially deployed and pin 1364 moves along opening 1362 toward longitudinal opening 1364 as shown in FIGS. 4A and 4B. Knob 1360 is further rotated and pusher arms 1324 moved distally until pin 1382 is aligned with longitudinal opening 1364 at which time spring 1384 expands and pushes pin 1382 proximally as shown in FIG. 5A. Since clip arms 1306 are fixedly attached to spring cylinder 1380, arms 1306 move proximally with pin 1382 to release the proximal portions of clips 1310 from clip pushers 1324 simultaneously. The deployed clips move toward or assume their memory shape set configuration, such as the loop shaped configuration shown in FIG. 5B. The mating threads on actuating knob 1360 and cylinder 1366 can be configured to facilitate deployment of all of the clips simultaneously upon one half turn of knob 1360.

Referring to FIGS. 6A-D, enlarged views of the distal portion of barb and clip arm pair is shown. FIG. 6A shows the distal portion of the arm pair before deployment of the barb or clip. FIG. 6B shows barb deployment. FIG. 6C shows the barb deployed and a clip partially deployed. FIG. 6D shows the barb deployed and arm 1306 retracted to fully deploy clip 1310.

In use, a tubular graft is everted over the distal ends of the barb-clip arm pairs. Barb actuator knob 1350 is rotated to extend all of the barbs simultaneously through their respective openings 1344 (FIG. 6B) to secure the graft to anastomosis device 1300 (see e.g., FIGS. 7A and 8A).

If the distal anastomosis (i.e., the anastomosis between the other end of the tubular graft structure "G" and a target coronary artery) has not yet been performed, then a cross-clamp is placed on the free end portion of the tubular graft structure to prevent blood leaking from the tubular graft structure.

Once this is completed the surgeon forms an opening "O" (FIG. 8A) in the aorta using, for example, a scalpel and an aorta cutting device such as an aortic punch (not shown). It should be understood that other known devices to form the opening also can be used. For example, a cylindrical member with a sharp cutting cylindrical edge with a piercing member positioned therein with an arrow type head to catch the cut tissue can be used. When the aortotomy or opening has been completed, the surgeon removes the cutter or punch and introduces the anastomosis device. More specifically, the anastomosis device is then positioned in an opening formed in a target tubular structure (e.g., an aorta) to which the tubular graft is to be anastomosed. The barbs sit on top of the target structure (e.g., around the opening formed in the aorta) and serve as a stop for the device. Spreader 1322 can be moved distally to expand the arms and form a seal between the tubular graft and the target structure. If the distal anastomosis was previously completed, blood can flow through the everted tubular graft structure to the coronary artery, thus revascularizing the heart.

Actuator knob 1360 is then rotated to begin deployment of the clips, which begin to return to their unconstrained closed shape or configuration (FIGS. 6C and 7B). FIG. 6D shows a further step in clip 1310 deployment. Knob 1360 is further rotated until pin 1382 is aligned with longitudinal opening 1364 at which time spring 1384 is allowed to expand toward its relaxed state and move pin 1364 proximally and clip tubes 1306 therewith. This exposes the proximal portions of clips 1310 and allows the clips, including their ball portions 1311, to pass through the openings or slots in pusher arms 1324 (FIG. 6D). Once deployed, released or ejected from arms 1306, self-closing clips 1310 return or move toward their memory set closed shape or configuration as described above and depicted in FIGS. 7C and 8B. At this point, knob 1350 is turned or rotated the other direction to retract barbs back into the barb arms 1340 so that the entire device can be removed from graft and target structure (e.g., an aorta) as shown in FIG. 8B.

As noted above, the devices described herein generally can be used to surgically connect structures in a patient. In a further example, they can be used to connect a generally circular object, such as a valve prosthesis, to an anatomic structure, such as a valve annulus. In the valve case, the barbs are passed through the outer annular portion or the sewing cuff of a valve prosthesis instead of an everted graft. The barb-valve prosthesis combination is then introduced through the space inside a patient's valve annulus and the clips positioned for ejection beneath the valve annulus. The clips are then ejected in a manner to pass through the valve annulus and the valve prosthesis so that as they are ejected they move toward their memory set closed configuration and secure the valve prosthesis to the valve annulus. The barbs can then be retracted and the device removed.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. Surgical connection apparatus comprising:
    a support structure, wherein said support structure comprises a first plurality of tubular members and second plurality of tubular members;
    a plurality of self-closing clips, each clip being, slidably disposed in one of said first plurality of tubular members, wherein the clips are configured to elect and release from the first plurality of tubular arms; and
    a plurality of barbs, each of the plurality of barbs being slidably disposed in one of said second plurality of tubular members, wherein a distal end of said each of the plurality of barbs is configured to extend from a distal portion of said each of second plurality of tubular members and retract back into said distal portion of said each of second plurality of tubular members.

2. The apparatus of claim 1 further including a first plunger movably coupled to said support structure and a pusher disposed in each of said first plurality of tubular members, each pusher having a proximal end being secured to said plunger and a distal end portion coupled to a respective clip so that movement of said plunger moves all of said clips therewith.

3. The apparatus of claim 2 wherein each clip has a memory set closed configuration, when said clips are disposed in said first plurality of tubular members each tubular member biases a respective clip away from said closed configuration, and when said clips are released from said tubular members said clips move toward their memory set closed configuration.

4. The apparatus of any one of claim 1 further including means for simultaneously deploying said clips.

5. The apparatus of claim 2 further including a second plunger movably coupled to said support structure, each barb having a distal end and a proximal end, said second plunger being coupled to each barb proximal end so that said second plunger moves all of said barbs therewith.

6. The apparatus of claim 1 wherein each barb has a distal portion with a memory set hook configuration, when said barb distal end portions are disposed in said second plurality of tubular members each tubular member biases a respective barb distal end portion away from said hook configuration, and when said barb distal end portions are extended away from said tubular members said barbs move toward their memory set hook configuration.

7. The apparatus of claim 1 further including means for simultaneously deploying said barbs.

8. The apparatus of claim 1 further including means for simultaneously deploying said clips and means for simultaneously deploying said barbs independently of said clips.

9. Surgical connection apparatus comprising:
    a support structure comprising a first plurality of arms and a second plurality of arms wherein the first plurality of arms forms a first plurality of paths and the second plurality of arms forms a second plurality of paths;
    a plurality of clips, each clip being slidably disposed in one path of the first plurality of paths, wherein the clips are configured to eject and release from the first plurality of arms; and
    a plurality of barbs, each of the plurality of barbs being longitudinally slidably disposed in one path of the second plurality of paths, wherein a distal end of each of the plurality of barbs is configured to extend from a distal portion of each of the second plurality of paths and retract back into the distal portion of each of the second plurality of paths, wherein the clips are separate from the barbs and are movable independently of the barbs and wherein the first plurality of arms and the second plurality of arms are arranged to form a plurality of arm pairs.

10. The apparatus of claim 9 further including a plunger movably coupled to said support structure and a pusher disposed in each of said first plurality of paths, each pusher having a proximal end being secured to said plunger and a distal end portion coupled to a respective clip so that movement of said plunger moves all of said clips therewith.

11. The apparatus of claim 10 further including a second plunger movably coupled to said support structure, each barb having a distal end and a proximal end, said second plunger being coupled to each barb proximal end so that said second plunger moves all of said barbs therewith.

12. The apparatus of claim 11 wherein said plungers are independently movable.

13. Surgical connection apparatus for connecting a first structure to a second structure, the connection apparatus comprising:

a support structure comprising a plurality of arm pairs, the plurality of arm pairs comprising a first plurality of tubular arms and a second plurality of tubular arms, a plurality of barbs coupled within the first plurality of tubular arms, wherein a distal end of each of the plurality of barbs is configured to extend from a distal portion of each of the first plurality of tubular arms and retract back into the distal portion of each of the first plurality of tubular arms, a plurality of clips being slidably coupled within the second plurality of tubular arms and independent of the barbs;

means for moving the barbs; and means for ejecting and releasing the clips from the second plurality of tubular arms.

14. The apparatus of claim 13 wherein said clips comprise shape memory material, have a memory set closed configuration, and move toward said closed configuration when ejected from said support structure.

15. The apparatus of claim 14 wherein said clip ejecting and releasing means ejects said clips simultaneously.

16. The apparatus of claim 13 wherein said clip ejecting and releasing means ejects and releases said clips simultaneously.

17. The apparatus of claim 16 wherein said barb moving means provides means for extending the barbs from said distal portion of each of the first plurality of tubular arms and retracting the barbs into said distal portion of each of the first plurality of tubular arms.

18. The apparatus of any one of claims 15-17 wherein said barb moving means moves said barbs simultaneously.

* * * * *